United States Patent [19]

Hahn et al.

[11] 4,276,144
[45] Jun. 30, 1981

[54] OXYGEN ELECTRODE AND METHOD FOR PREPARATION THEREOF

[75] Inventors: Allen W. Hahn; Michael F. Nichols, both of Columbia; Ashok K. Sharma, Rolla; Eckhard W. Hellmuth, Kansas City, all of Mo.

[73] Assignee: The Curators of the University of Missouri, Columbia, Mo.

[21] Appl. No.: 123,091

[22] Filed: Feb. 20, 1980

[51] Int. Cl.³ .................. G01N 27/30; G01N 27/40; B05D 3/14
[52] U.S. Cl. .................. 204/195 P; 128/635; 204/32 R; 204/38 A; 427/41; 427/255.6
[58] Field of Search .............. 204/195 P, 1 P, 38 A, 204/32 R; 427/41, 255.6; 128/635

[56] References Cited

PUBLICATIONS

Michael L. Hitchman, "Measurement of Dissolved Oxygen", Chap. 4, pp. 59-70, (1978).
I. A. Silver et al., "Oxygen Transport to Tissue-III", pp. 9-14, (Plenum Press), (date unknown).
V. G. Murphy et al., Biomedical Sciences Instrumentation, vol. II, pp. 31-36, Apr. 1975.
Ashok K. Sharma et al., J. Appl. Physics, 49, 10, pp. 5055-5059, Oct. 1978.
H. Yasuda et al., J. Polymer Science: Polymer Chemistry Edition, vol. 16, p. 743, (1978).
H. Yasuda, "Glow Discharge Polymerization", pp. 361-398, vol. IV-2, (Academic Press, Inc.), (1978).
A. W. Hahn et al., "Plasma-Formed Polymers for Biomedical Applications", NBS Spec. Pub. 415, pp. 13-17, (1975).
K. G. Mayhan et al., "Plasma-Formed Polymers for Biomedical Applications", NBS Spec. Pub. 415, pp. 1-12, (1975).
K. G. Mayhan et al., "A New Approach to Coating Oxygen Electrodes", 25th ACEMB, Oct. 1-5, 1972.
T. E. Tang et al., J. of Bioengineering, vol. 2, pp. 381-388, (1978).

*Primary Examiner*—G. L. Kaplan
*Attorney, Agent, or Firm*—Senniger, Powers, Leavitt and Roedel

[57] ABSTRACT

An oxygen electrode adapted for use for polarographic, galvanometric or amperometric analyses, that is resistant to poisoning and effective for accurate, reproducible current and voltage measurements. The electrode comprises a conductor constituted of a metal which catalyzes the cathodic reduction of oxygen, an electrical lead electrically connected to the conductor, and an insulating jacket covering all of the conductor except a working surface thereof that is adapted to communicate with an oxygen-containing environment for the cathodic reduction of oxygen. The conductor has a layer of an oxide of the aforesaid metal at its working surface. There is a thin polymeric coating over said oxide layer and securely adhered to the working surface. The coating comprises a polymer produced by glow discharge polymerization of an aliphatic hydrocarbon and has such properties to permit the reduction of oxygen at the electrode by electrons supplied at the working surface through the lead and conductor.

A method for preparing the electrode is also disclosed.

37 Claims, 13 Drawing Figures

OXYGEN ELECTRODE AND METHOD FOR PREPARATION THEREOF

BACKGROUND OF THE INVENTION

This invention relates to the field of electrochemical analytical instruments and, more particularly, to an improved oxygen electrode which provides consistent, reproducible and reliable signals and is resistant to poisoning by certain ions or by the components of biological systems.

When used as a cathode in a polarographic, galvonometric or amperometric analytical system, an oxygen electrode is effective for the reduction of oxygen in its environment and provides a current or voltage output which is a function of the oxygen concentration in that environment. Oxygen electrodes are constructed of conductors such as platinum or gold which catalyze the cathodic reduction reaction. Under a negative voltage of 0.3-0.8 volts with respect to a saturated calomel electrode, oxygen may be reduced at a bare platinum electrode, for example, in accordance with the following reaction:

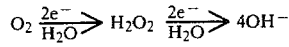

$$O_2 \xrightarrow[H_2O]{2e^-} H_2O_2 \xrightarrow[H_2O]{2e^-} 4OH^-$$

In certain environments, most particularly the biological systems whose oxygen content such electrodes are often used to measure, the electrode "ages" rapidly and loses its ability to catalyze the second step of the four electron reduction set forth above. The electrode reaction thus becomes increasingly limited to the two electron reduction illustrated in the first step of the equation and the current output declines.

While the shift from four electron to two electron transfer would not present a serious obstacle to reproducible analyses if the shift were consistent, quantitative and predictable, the available oxygen electrodes have exhibited a proclivity for random shifts in their current outputs both upward and downward. As a consequence, their practical utility for measuring oxygen concentrations (without recourse to frequent recalibrations) has been rather limited.

In addition to the shifts in current output resulting from electrode aging, the progress of the oxygen reduction reaction taking place at the electrode is adversely affected by various poisons. Certain ions are poisons and the macromolecules contained in biological systems have a further unfavorable impact on the predictability and reproducibility of operation of oxygen electrodes. Proteins, in particular, are known poisons for oxygen electrodes and those proteins containing sulfur bearing amino acids are especially deleterious.

In an effort to avoid such aging and poisoning problems, the so-called Clark electrode has been developed in which a glass insulated platinum conductor is immersed in a standard electrolyte that is in turn contained within a membrane that separates the standard electrolyte and conductor from the environment in which it is used. The membrane has such diffusional properties as to permit measurement of the oxygen content of the electrode's environment. However, the Clark electrode is somewhat bulky, has a relatively sluggish response, and is not particularly well adapted for the long-term measurement of intravascular oxygen content or the oxygen content of tissue.

Efforts have also been made to protect oxygen electrodes from poisoning by dip coating the sensor in a polymeric material and allowing it to dry. However, it is very difficult to obtain a precise or uniform coating by a dipping technique, and the polymers that have been available for use therein have been susceptible to peeling away from the electrode surface. Moreover, the membranes produced by dip coating, and those utilized in Clark electrodes, have been relatively thick, thereby extending the response time by inhibiting the transport of oxygen to the sensing surface. As described in Hahn et at., "Plasma-Formed Polymers for Biomedical Applications Part II. Biocompatibility and Applications," National Bureau of Standards Special Publication 415 (May 1975), attempts have also been made to provide a membrane over a platinum-iridium oxygen electrode through deposition of a polymer coating by glow discharge polymerization. However, the coatings produced in that work were relatively thick, gave unsatisfactory electrochemical responses and prematurely peeled away from the metal electrode surface.

SUMMARY OF THE INVENTION

Among the several objects of the present invention, therefore, may be noted the provision of an improved oxygen electrode for use in polarographic, galvanometric and amperometric determinations; the provision of such an electrode which affords reliable performance; the provision of such an electrode which is highly sensitive and affords short response time; the provision of such an electrode which can be produced in miniature for use in intramuscular, intravascular and other biological applications; the provision of such an electrode which provides reproducible results, more particularly resistance to aging drift and poisoning; the provision of such an electrode which is generally compatible with biological systems; the provision of such an electrode which can be handled without abrasion or other damage to key components; and the provision of a method for producing an electrode of the aforesaid type.

Briefly therefore, the present invention is directed to an oxygen electrode that is adapted for use in polarography, galvanometry and amperometry, and is resistant to poisoning and effective for accurate reproducible current and voltage measurements. The electrode comprises a conductor constituted of a metal which catalyzes the cathodic reduction of oxygen, an electrical lead electrically connected to the conductor, and an insulating jacket covering all of the conductor except a working surface thereof that is adapted to communicate with an oxygen-containing environment for the cathodic reduction of oxygen. The conductor has a layer of an oxide of the aforesaid metal at the working surface and a thin polymeric coating over the oxide layer and securely adhered to said surface. This coating comprises a polymer produced by glow discharge polymerization of an aliphatic hydrocarbon and has such properties as to permit reduction of oxygen at the electrode by electrons supplied at the surface through the lead and the conductor.

The invention is further directed to a method for producing an oxygen electrode that is adapted for use in polarography, galvanometry or amperometry, and is resistant to poisoning and effective for accurate reproducible current and voltage measurements. In the method, a plasma is generated from an inert gas in a low pressure chamber containing the working surface of an oxygen electrode. The electrode comprises a conductor constituted of a metal which catalyzes the cathodic reduction of oxygen and an insulating jacket that covers all of the conductor except the working surface that is adapted to communicate with an oxygen-containing environment for the cathodic reduction of oxygen. The conductor has a layer of oxide on the metal at the working surface. An aliphatic hydrocarbon gas is introduced into in the chamber and the hydrocarbon is polymerized by action of the plasma thereon. A thin adherent coating of the polymer is deposited over the oxide layer at the working surface.

Other objects and features will be in part apparent and in part pointed out hereinafter.

BRIEF DESCRIPTION OF THE DRAWINGS

Corresponding reference characters indicate corresponding parts throughout the several views of the drawings.

DESCRIPTION OF THE PREFERRED EMBODIMENT

Figure 1:
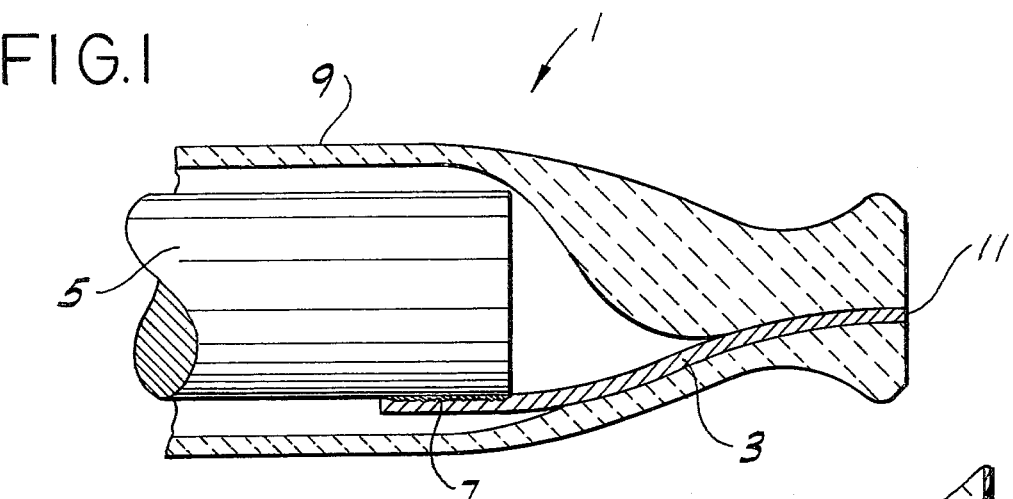
FIG. 1 is an enlarged side elevation of the working end of the electrode of the invention having a glass insulating jacket that is shown in section to better illustrate the components of the electrode.
Figure 2:
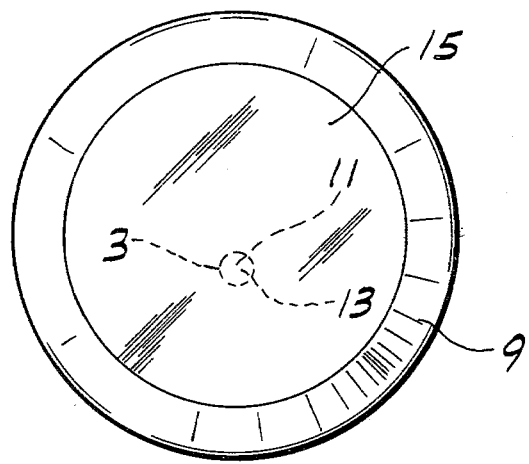
FIG. 2 is an end view of the electrode of FIG. 1 illustrating the relative size of the wire conductor and the glass insulating jacket.
Figure 3:
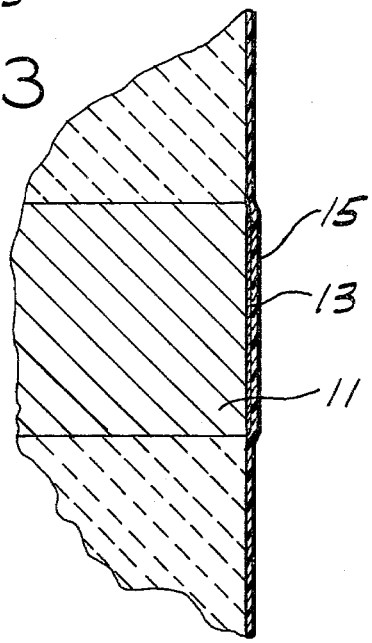
FIG. 3 is a greatly enlarged broken away sectional view of the working end of the conductor and immediately surrounding portions of the insulating jacket, illustrating the oxide layer on the working surface and the adherent polymer layer thereover.

Referring to FIG. 1–3 of the drawings there is shown an oxygen electrode 1 which comprises a conductor wire 3 constituted of a metal which catalyzes the cathodic reduction of oxygen. Electrically connected to wire 3 is a lead wire 5, typically of copper. The electrical junction 7 between conductor 3 and lead 5 is typically provided by silver soldering or ultrasonic welding. A glass insulating jacket 9 surrounds junction 7 and covers all of conductor 3 except a working surface 11 at a crossectional face of the conductor on the end thereof opposite from junction 7. Exposed working surface 11 is thus adapted to be in communication with an oxygen-containing environment for the cathodic reduction of oxygen. At working surface 11 is a layer 13 comprising an oxide of the metal constituting wire 1. Over oxide layer 13 is a thin coating 15 that is produced by the glow discharge polymerization of an aliphatic hydrocarbon. Coating 15 is securely adhered to surface 11 and the surrounding portions of jacket 9 and has such properties as to permit the reduction of oxygen at the electrode by electrons supplied at surface 11 through lead 5 and conductor 3.

Utilizing the method of the invention as described hereinbelow, electrode 1 can be produced in miniature so that it is adapted for intramuscular, intravascular or other biological applications. For example, the electrode can be produced from a platinum conductor wire having a diameter less than 100 $\mu$m, conveniently about 50 microns, attached to a 20 gauge copper wire lead and contained within a glass jacket having an overall diameter of less than 1.5 mm. The electrode can be constructed in larger sizes for various industrial applications.

Any metal which is effective for catalyzing the cathodic reduction of oxygen can be used as the constituent metal of conductor 3. For biological applications, the conductor is advantageously constructed of a metal which is compatible with biological environments. Preferably the conductor comprises platinum, with 99.99+% pure platinum being most preferred. Other metals which can be used for the conductor include gold, palladium, tantalum and iridium.

Lead wire 5 can be constituted of any conductive material which is readily joined to the material of conductor 1. Copper is most preferred. Insulating jacket 9 is preferably a relatively soft glass which can be drawn and sealed by exposure to a burner flame. There are otherwise no critical requirements as to the composition of the glass. Junction 7 is conveniently contained within glass jacket 9 as illustrated, but may be alternatively located outside the glass provided that the jacket includes some other insulating material, for example, epoxy, which seals the end of the glass and surrounds any portion of the conductor and lead wire that may be exposed to the conductive medium in which measurement is to be made.

Oxide layer 13 is produced by anodizing working surface 11. The presence of this oxide layer contributes consistency and reproducibility to the initial response of the electrode in making analyses based on oxygen reduction. In the case of a platinum conductor, the oxide layer is preferably constituted predominantly of PtO.

Coating 15 is produced by polymerization of an aliphatic monomer in a low pressure gas plasma. Because visual range electromagnetic radiation emanates from the plasma, it is referred to as a glow discharge system and the polymerization technique is thus defined as glow discharge polymerization. As a result of the ionizing capacity of the gas plasma system, not only olefinic hydrocabons but low molecular weight alkanes can be polymerized by the glow discharge technique. Thus, for example, polymeric coating 15 can be constituted of glow discharge polymerized ethylene, propylene, butene, methane, ethane, propane or butane. Such polymers are highly crosslinked and have a relatively high density as compared to polyolefins prepared by conventional addition polymerization. For example, glow discharge polymerized polypropylene has a density of 1.11 g/cc and a refractive index of 1.540 while conventional polypropylene has a density of 0.90 g/cc and a refractive index of 1.49. As a result of the differing polymerization mechanisms, not only the physical properties but also the chemical composition of glow discharge polymerized propylene differ from the conventional polyolefin. Moreover, because of the highly activated condition of the monomer from which it forms, the polymer undergoes a slight degree of reaction with oxygen upon exposure to air after removal from the polymerization system. Thus, a glow discharge polymerized propylene coating which typically conforms to the average empirical formula:

$$(C_1H_{1.59}O_y)$$

where y ranges up to 0.2 depending on the age of the polymer. By contrast, conventional polypropylenes conforms to the structural formula:

$$-(CH_2-CH-)_n$$
$$\phantom{-(CH_2-}|$$
$$\phantom{-(CH_2-}CH_3$$

where n equals the number of repeating units.

By proper control of the polymerization conditions and time, coating 15 is made ultrathin. As a consequence of its thin dimension and structure, the polymer is securely adhered to working surface 11 and the surrounding portions of jacket 9 and the coating possesses such properties whereby oxygen may be reduced at the electrode by electrons supplied at the working surface. Thus, for example, the coating can be as thin as 500 Angstroms and should preferably be no thicker than approximately 0.3 $\mu$m. It has been discovered that thicker coatings are of limited adherence and cause the electrode to exhibit rather erratic current/voltage characteristics. Thus, the presence of such thick coatings was apparently responsible for the unsatisfactory performance of the electrodes described in the aforesaid paper of Hahn et al. For satisfactory adhesion, it has also been found that the proportion of hydrogen in the above-noted empirical formula the for propylene polymer should be at least about 1.4.

The use of a thin polymer coating affords the further advantage of very rapid response time. A thickness in the range of approximately 0.1 to 0.15 $\mu$m is considered to be near the optimum for the coating. By use of the glow discharge polymerization technique, it is possible not only to carefully control the average thickness of coating 15 but also to produce a coating whose thickness is highly uniform and conforms closely to the shape or contour of surface 11. Moreover, the ultrathin film adheres very securely to the oxidized surface and is resistant to peeling, development of pinholes or deterioration. Despite its thin dimension the polymer coating is also resistant to abrasion so that the electrode can be handled and inserted into body tissue without adverse effect on its performance properties. Additionally, the coating is resistant to chemical or physical attack by either the environment in which it is used or exposure to light. It is further compatible with biological systems causing no significant foreign body reaction.

Most significantly, it has been discovered that the presence of a polymeric coating of the character of coating 15 eliminates both age and poisoning drift of the oxygen electrode. Although we do not wish to be held to a particular theory, it appears that the polymer coating is sufficiently dense to limit oxygen reduction to the two electrode reaction so that there is no shift back and forth between the four-electron and two-electron current, a shift which may partly account for the random drift experienced in conventional oxygen electrodes. The coating also serves as a semipermeable membrane to screen out macromolecular species such as proteins which may otherwise cause poisoning of the electrode. On the other hand, the properties of the ultrathin glow discharge polymerized coating are adequate to provide a measurable two electron transfer current which is effective for polarographic determination of oxygen concentration as well as for galvanometric and amperometric measurements in oxygen-containing environments. These properties may result either from permeability of the coating to diffusion of oxygen and electrolytic reaction products, or to transfer of electrons through the coating with reaction occurring at the polymer surface. Conceivably a combination of both phenomena is involved.

The favorable properties of the coating arise in significant part from the controlled uniform thickness, adherence and conformance to the underlying surface. It is also believed, however, that the dense cross-linked polymer structure contributes to a favorable balance of charge transfer properties. Thus the polymer structure is believed to inhibit four electron transfer and ingress of poisoning agents, yet possess adequate charge transfer properties to facilitate a predictable and reproducible oxygen concentration-responsive two electron reaction.

Figure 4:
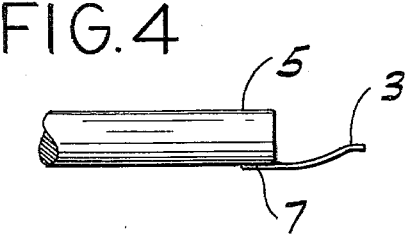
FIGS. 4–6 illustrate the method of construction and assembly of the electrode of the invention.
Figure 5:
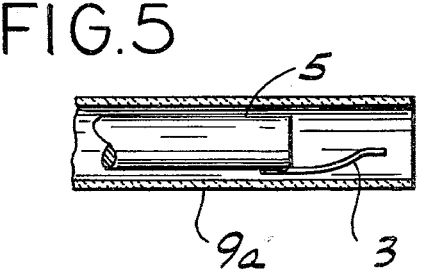
Figure 6:
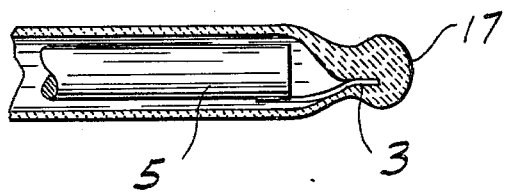

According to the method of the invention, one end of a conductor wire 3 is initially bonded to a lead wire 5 as illustrated in FIG. 4. To provide a mechanically secure low electrical resistance bond, the junction 7 between wire 3 and lead 5 may be effected by silver soldering, ultrasonic welding etc. The platinum wire is also flame treated to eliminate surface contaminating dirt, oils etc. As illustrated in FIG. 5, a soft glass capillary tube 9a is then slid over the joined conductors and the end of the tube containing the free end of conductor 3 is heated in a miniature oxyacetylene flame while the tube is carefully rotated so that glass flows around the free end of the conductor to form a tight glass/metal seal (FIG. 6).

The bulbous end 17 of sealed glass which forms over the free end of conductor wire 3 is polished off to expose only a circular crosssectional disk-like face of the conductor, which is otherwise completely covered by glass insulating jacket 9 that also surrounds junction 7. Polishing is carried out with progressively finer grits of a common laboratory abrasive such as aluminum oxide. The wire face exposed by polishing serves as working surface 11 of the electrode. The assembled and polished construction conforms to that illustrated in FIGS. 1 and 2 except for the oxide layer and a polymeric coating which are provided in accordance with the steps described hereinbelow.

Before anodization, the free end of lead 5 is fitted with an appropriate electrical connector which is used as a current pathway in both the anodization step and in the ultimate service application of the electrode. The end of jacket 9 opposite from working surface 11 of the electrode is sealed, for example, by uase of an epoxy compound. Working surface 11 is then cleaned and is ready for anodization.

Anodization is effective to conform the sensing surface to a standard state wherein electrode to electrode variance is minimized with respect to initial current/voltage response. Anodization also minimizes electrode to electrode variance in age drift but does not eliminate that phenomenon. Anodization is conducted in a strong oxidizing electrolyte that is substantiallly free of chloride ions. Thus, for example, sulfuric acid,, nitric acid or potassium dichromate may be used, with a sulfuric acid solution having a concentration of 0.5–2.0 N being preferred. For a sulfuric acid electrolyte of this type, anodization may be typically carried out at a D.C. voltage of 1–4 volts for a period of 30 seconds to 5 minutes. After anodization, the electrode is again cleaned prior to glow discharge deposition of the polymer coating 15.

Figure 7:
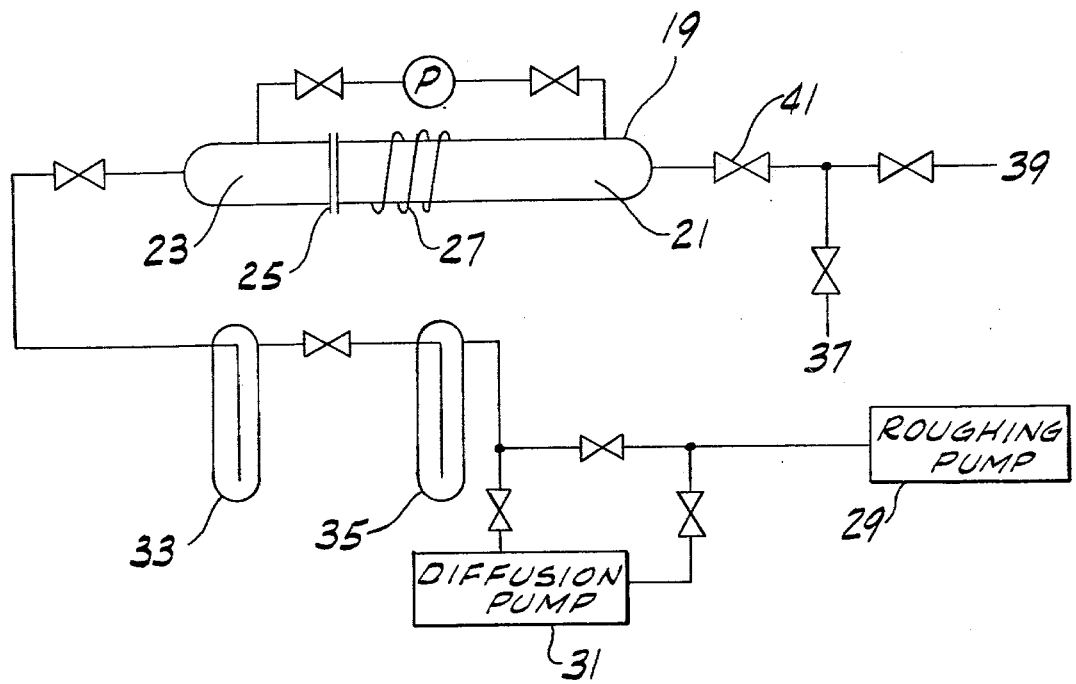
FIG. 7 is a schematic diagram showing a process by which glow discharge polymerized aliphatic hydrocarbon may be deposited on the working surface of the electrode.

Deposition of the polymer coating may be conducted using a system of the type described in FIG. 7. Shown at 19 is a tubular reactor comprising a reaction chamber 21 and a head 23 detachably connected to chamber 21 by a flanged connection 25. A coil 27 is disposed in proximity to chamber 21 for generation of plasma therewithin. The reactor may be evacuated by use of roughing pump 29 and a high vacuum created in the reactor by diffusion pump 31 operating in conjunction with cold traps 33 and 35 which are cooled with liquid nitrogen. Argon or other inert gas may be introduced into the system from inert gas supply 37 while hydrocarbon monomer is delivered to the reactor from supply 39 through leak valve 41.

Preparatory to the coating step, the electrodes are each completely wrapped in aluminum foil except for the tip thereof which is exposed for deposit of polymer coating thereon. A series of electrodes are placed on a ceramic holder which is adapted to rest within the reaction chamber. Head 23 is removed to permit insertion of the holder in chamber 21 and then replaced. After the head is replaced, roughing pump 29 and diffusion pump 31 are operated to evacuate reactor 19 and reduce the absolute pressure as low as practical. An inert gas such as argon from supply 37 is bled into the low pressure chamber within reactor 19 where it is inductively coupled to coil 27 operated to introduce electromagnetic energy into the gas. Plasma formation is initiated, and induction coil 27 is operated to continue generation of the plasma. The induction coil may be operated over a wide range of frequencies, from as low as 1 kilohertz to approximately 40,000 megahertz. Preferably the frequency is within the RF range.

By collision of hydrocarbon monomer with the ions and electrons of the plasma within the reactor chamber, free radicals are produced which initiate and propagate polymerization of the monomer and produce a polymer which is deposited on all surfaces within the reactor chamber, including oxide layer 13 on working surface 11 of each electrode contained therein. During the reaction, the pressure is preferably maintained at between about 10 and about 30 pascals by operation of the diffusion pump. The plasma is maintained by continued introduction of electromagnetic energy through the inductive coupling effected by continued operation of coil 27. It has generally been found that a balance between power input into the reaction chamber and the flow rate of monomer must be maintained to insure deposit of the polymer on the surface of the electrode rather than precipitating it in the gas stream to form a "snow". To produce a tightly adherent polymer coating having the desired electrolytic properties, the power output of the frequency generator in the case of a tubular reactor should be controlled at between about 0.2 and about 0.9 KWH per gram of monomer continuously fed to the reaction zone. For maximum adherence, it is also preferred that the feed rate be controlled so that the deposition rate is such as to build the thickness of the polymer layer at a rate of between about 25 and about 40 Angstroms/min. Proper control can be recognized in part by visual observation, and is generally associated with a glow discharge envelope which is coextensive with the zone within which the polymer deposit is desired. Thus, at the desired monomer flow rate, power to the coil can be adjusted to maintain such an envelope.

It will understood that configurations other than tubular may be utilized for the reaction chamber. For example, the reaction may be carried out in a Bell jar or other vessel suitable for high vacuum operation. Also the plasma may be produced by means other than inductive coupling, for example, by capacitive coupling. Where the reactor has the geometry of a Bell jar, the power required is between about 5 and about 15 KWH/g.

Prior to introduction of monomer into the glow discharge chamber, it is advantageous to clean and etch the oxidized working surface of the electrode by briefly subjecting it to inert gas sputtering in the plasma. Such treatment further promotes adherence of the polymer coating to the oxide layer on the sensing surface. Subsequent to deposition of the polymer coating, it is sometimes useful to bleed in air or oxygen at low pressure and establish an oxygen plasma with which the outer surface of the polymer coating may be etched. The latter etch is believed to tie up free radicals generated in the polymerization process and thereby make the film more stable. It also contributes hydrophilicity to the polymer surface, thereby promoting the hydration of the polymeric coating that is necessary to put the electrode in working condition.

The following example illustrates the invention.

EXAMPLE

A short (1 cm) segment of platinum wire (99.999% Pt.) having a diameter of 50 microns was bonded by silver soldering at one end thereof to a longer segment of 22 gauge copper wire. A glass capillary tube was slid over the platinum wire and the junction between the platinum and copper wires. At the free end of the platinum wire the capillary glass tube was fired with a miniature oxy-acetylene torch while the wire and glass assembly was rotated to minimize radial thermal gradients at the end being fired. Firing caused the glass to be drawn down over the platinum wire to encapsulate it. The fired end of the glass tube was then polished to expose a circular crossection of metal at the end of the platinum wire. The other end of the capillary was sealed with an epoxy compound. The electrode thus produced was ultrasonically cleaned in glass distilled water for 10 minutes, in ethanol for 5 minutes, and again in glass distilled water for 5 minutes. After cleaning, the exposed end of the platinum wire was anodized in 1 N sulfuric acid for 2 minutes at 2 volts D.C. (vs. a platinum wire of a larger diameter) at an electrode gap of 2 cm., and anodization was followed by ultrasonic cleaning in glass distilled water for 10 minutes. The electrode was then cathodized for 5 minutes in 0.9% saline solution and a polarogram recorded after the current had stabilized. Thereafter, the ultrasonic cleaning operation in water, ethanol and water was repeated and the electrode allowed to dry in a clean environment.

The exposed working surface of the platinum wire was coated with glow discharge polymerized propylene in an inductively coupled tubular reactor system of the type illustrated in FIG. 7. The entire electrode assembly except the tip was covered with aluminum foil and mounted in an electrode holder which carried two other electrodes of the same type and was provided with loops for holding the electrodes along the axis of the reactor. Head 23 of the reactor was detached at flanged connection 25 and the electrode holder carrying the electrodes was positioned within the reaction chamber. After the head was re-attached, the chamber was evacuated using roughing pump 29 and the total pressure within the chamber reduced to less than 0.1 pascal by operation of diffusion pump 31 in conjunction with cold traps 33 and 35. Argon was bled in from inert gas supply 37 and a plasma was created within reactor 19 by operation of coil 27 at a frequency of 27.1 megahertz and a power input of 100 watts.

Prior to the introduction to monomer, the electrodes were etched for 20 minutes by argon sputtering. Propylene from monomer supply 39 was then introduced through leak valve 41 at a flow rate of 340±10 μmoles per minute for a period of 30–150 minutes. Deposition was terminated when the thickness of the polymer film reached 0.1 μm. Additional runs were carried out producing electrodes having polymeric film coatings with thicknesses of 0.15 μm and 0.3 μm, respectively.

Electrodes produced in accordance with this example were placed in a 0.9% by weight saline solution and subjected to polarization at room temperature. The polarization runs were conducted in a Faraday cage in order to minimize electrical noise. The electrodes were connected to an electrometer amplifier whose output was coupled to both a strip recorder and an A to D converter connected to a PDP 11/03 computer. Data presented were plotted on a Calcomp Plotter under computer control.

Figure 8:
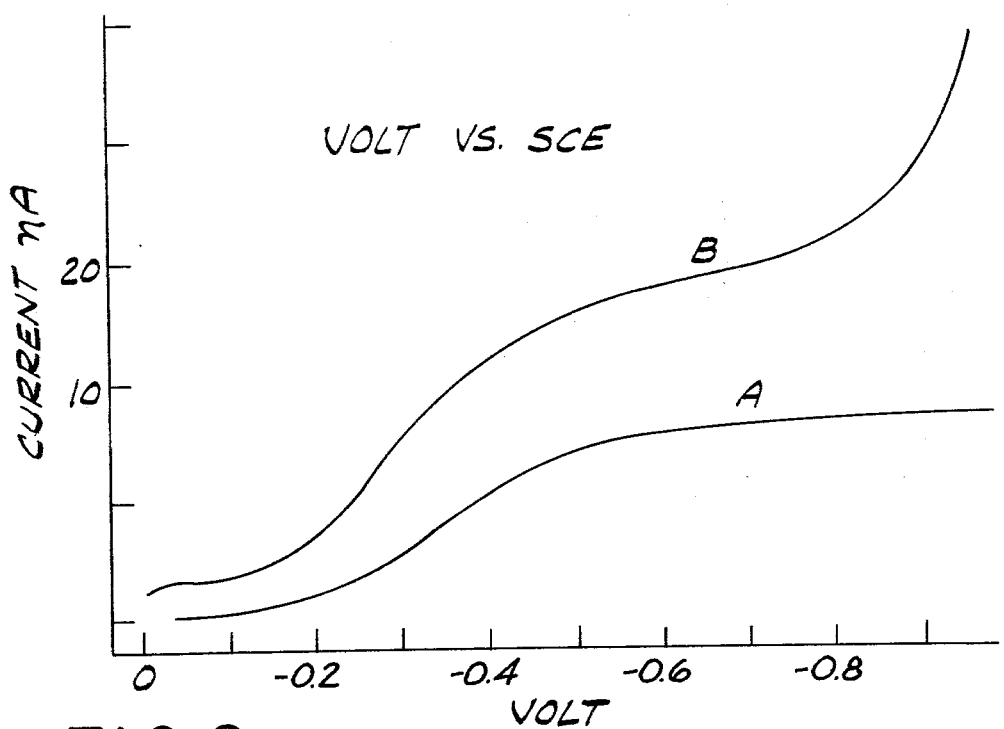
FIG. 8 is a plot comparing the current/voltage curves for the reduction of oxygen in an air-saturated 0.9% sodium chloride solution using an uncoated electrode and the electrode of the invention having a 0.15 $\mu$m thick mircon glow discharge polymerized propylene coating over an anodized conductor.

Polarograms were also obtained on oxygen electrodes which lacked the polymeric coating of this example but which were in all other respects identical to the electrodes thereof. Set forth in FIG. 8 are the comparative polarographic current/voltage curves for reduction of oxygen at both coated and uncoated platinum wire electrodes in an air saturated 0.9% sodium chloride solution using a standard calomel electrode as a reference. Curve B shows the current response for the uncoated electrode and curve A shows the response for the same electrode having a coating of approximately 0.15 microns of glow discharge polymerized propylene. Curve A exhibits a lower current indicative of the probable limitation of its operation to two electron transfer. It also has a flatter slope and more extended plateau region which renders the reproducibility of oxygen concentration measurements less vulnerable to small variations in applied voltage.

Figure 9:
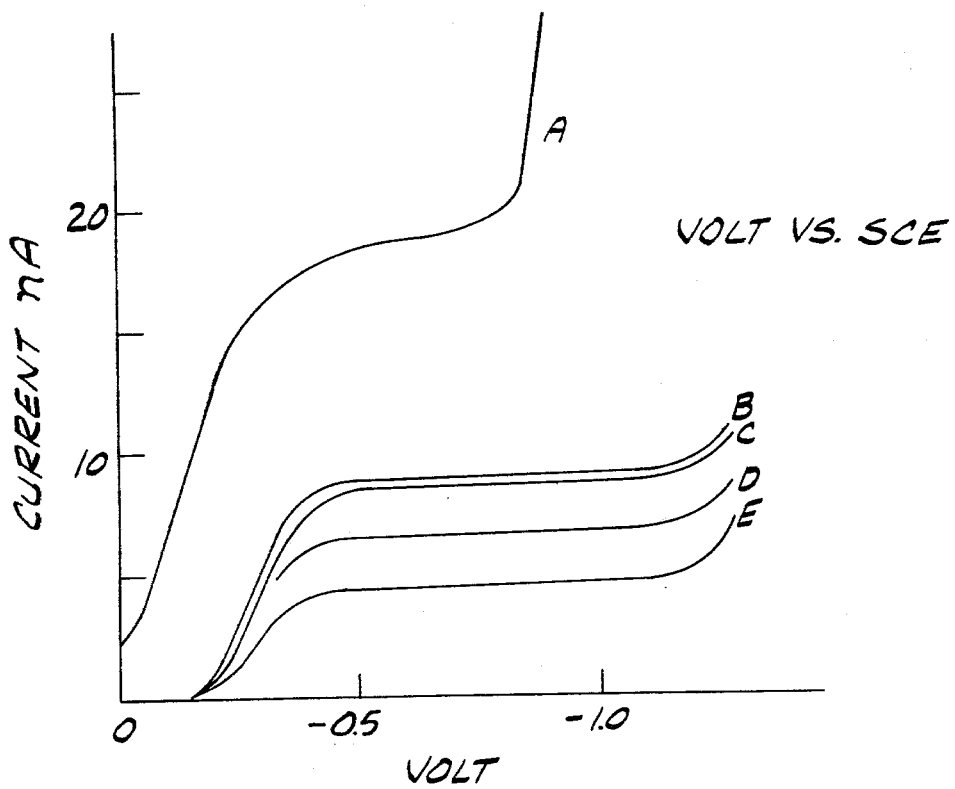
FIG. 9 shows a series of cathodic polarograms for the reduction of oxygen at platinum wire microelectrodes in 0.9% saline solution, curve A of which is for an uncoated electrode in a solution saturated with air and curves B–E of which are for electrodes having a 0.1 $\mu$m thick glow discharge polymerized propylene coating over an anodized conductor at varying concentrations of oxygen in the saline solution.

FIG. 9 shows polarograms for another series of platinum wire microelectrodes in 0.9% saline solutions. Curve A is for an uncoated electrode whereas curves B, C, D and E are for electrodes of this example having a 0.1 micron thick low discharge polymerized propylene coating. Curve B shows the current response for a solution saturated with gas containing 21% oxygen, curve C is for a solution saturated with air, curve D is for a solution saturated with a gas containing 15% oxygen and curve E is for a solution saturated with a gas containing 10% oxygen. The coated electrode plots of FIG. 9 reflect the same apparent two electron transfer limitation for the coated electrode and each include an extended plateau region which is conducive to accurate and reproducible measurement of oxygen concentration.

Figure 10:
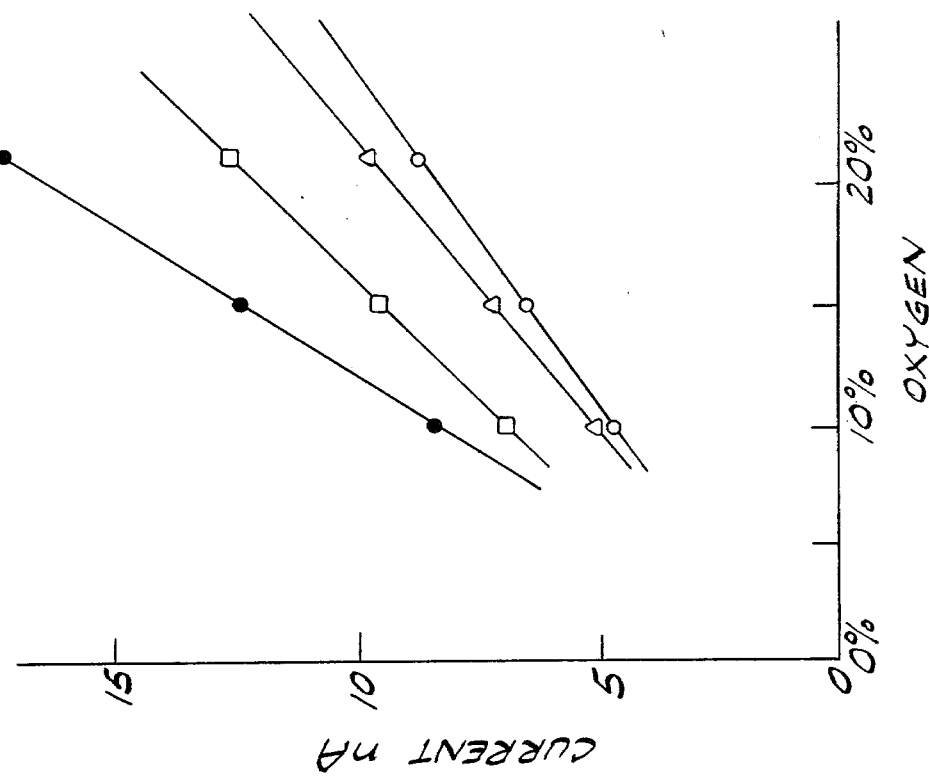
FIG. 10 shows a series of curves plotting the current response vs. the oxygen content of 0.9% saline solution for platinum microelectrodes having a 0.1 micron thick glow discharge polymerized propylene coating over an anodized platinum surface at a cathodization voltage of 500 mv. with respect to a saturated calomel electrode, each curve representing an electrode which had been stored for a designated period of time prior to testing.

FIG. 10 shows a series of curves which plot current against oxygen content for electrodes which were aged for varying period in 0.9% sodium chloride solution. Each of the electrodes was produced in accordance with this example and had a 0.1 micron thick glow discharge polymerized propylene coating on the working surface thereof. Not only are the curves highly linear but there is very little shift of the slope or intercept of the curves as a function of the time for which they were stored.

Figure 11:
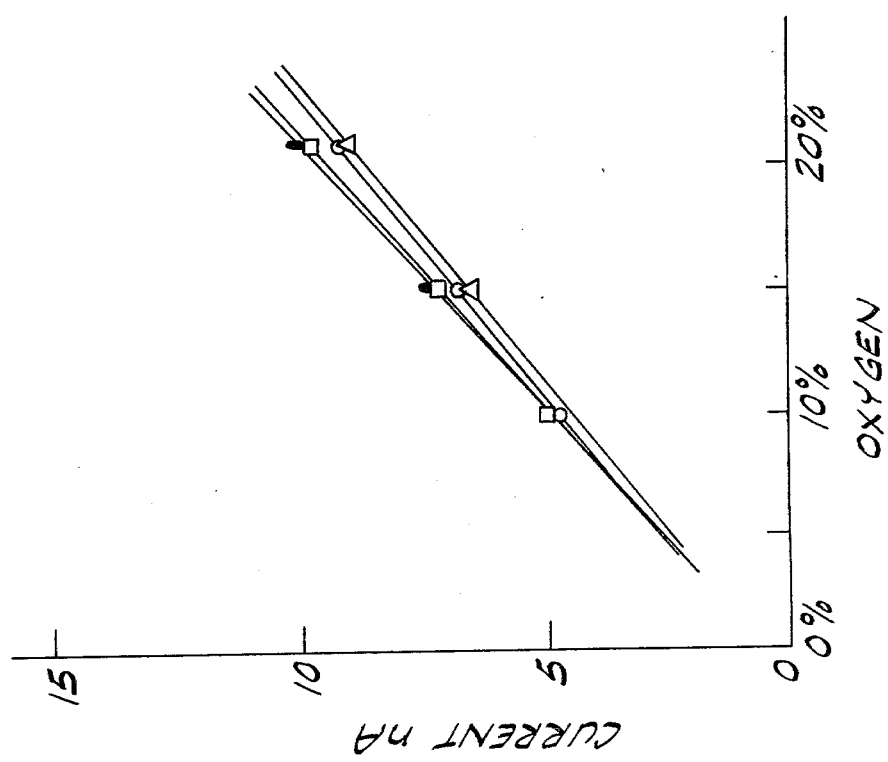
FIG. 11 shows a series of curves comparable to those of FIG. 10 but for electrodes having a 0.3 micron thick glow discharge polymerized propylene coating.

FIG. 11 is a plot similar to that of FIG. 10 except that the glow discharge polymerized propylene coating on the oxygen microelectrode had a thickness of 0.3 microns instead of 0.1 microns. Again the curves remained linear but storage for more than about 35 days was associated with a marked increase in slope, indicating loss of the integrity of the coating and return to bare surface condition.

A further series of runs was made to determine the initial current shift and protein poisoning of both coated and uncoated oxygen wire electrodes. Under a polarization voltage of −700 millivolts (vs. a standard calomel electrode) the output currents of these electrodes were first monitored for up to 36 hours. After this initial run the polarization curves were repeated and the electrodes were again allowed to run under the same constant polarization voltage for 16 hours in 0.9% saline. At that juncture bovine serum albumin was added to induce electrode poisoning and current monitoring was thereafter continued for an additional 12–20 hours. A Keithly model 416 picoammeter and multipoint recorder were used for this purpose.

Figure 12:
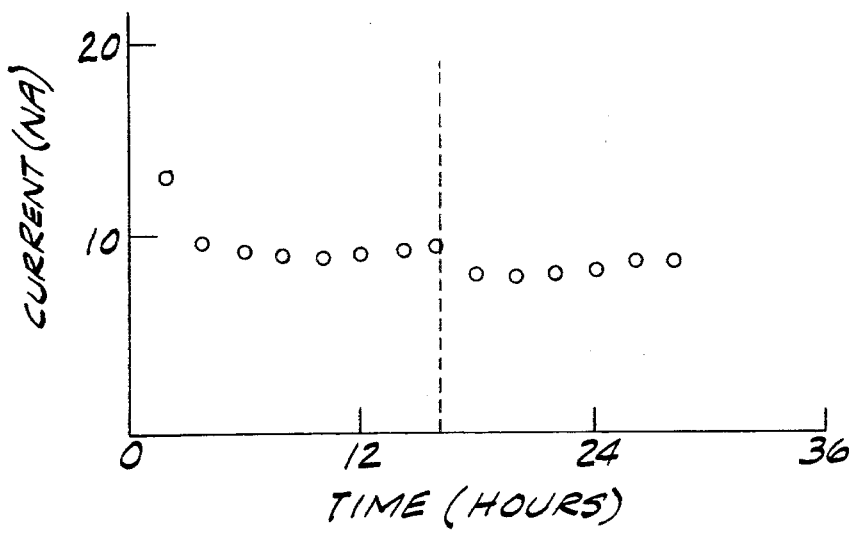
FIG. 12 illustrates the current response as a function of time, and as affected by the addition of bovine serum albumin, for an uncoated platinum oxygen sensing electrode at 0.9% saline solution saturated with air using a standard calomel electrode as a reference.
Figure 13:
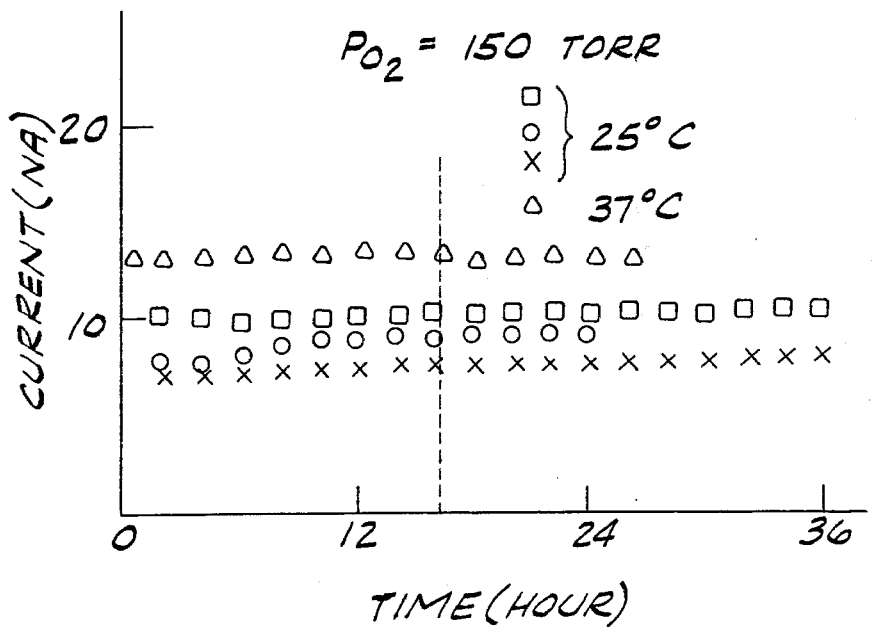
FIG. 13 is a plot showing current as a function of time, and as affected by the addition of bovine serum albumin, for a series of platinum electrodes having 0.1 $\mu$m thick coatings of glow discharge polymerized propylene is 0.9% saline solution at varying temperatures.

Shown in FIG. 12 and 13 are plots of current versus time for these runs. In the plot of FIG. 12 it may be seen that the initial current is relatively high, apparently reflecting at least partial four electron transfer, and that this current decays rapidly with aging. FIG. 12 further reflects a distinct poisoning effect upon introduction of bovine serum albumin. By contrast, all of the plots of FIG. 13 reflect a constant current output unaffected by either aging or poisoning. FIG. 13 includes a series of plots for different conditions of temperature.

In view of the above, it will be seen that the several objects of the invention are achieved and other advantageous results attained.

As various changes could be made in the above methods and products without departing from the scope of the invention, it is intended that all matter contained in the above description or shown in the accompanying drawings shall be interpreted as illustrative and not in a limiting sense.

What is claimed is:

1. An oxygen electrode, adapted for use in polarography, galvanometry or amperometry, that is resistant to poisoning and effective for accurate, reproducible current and voltage measurements, comprising a conductor constituted of a metal which catalyzes the cathodic reduction of oxygen, an electrical lead electrically connected to said conductor, an insulating jacket covering all of said conductor except a working surface thereof that is adapted to communicate with an oxygen-containing environment for the cathodic reduction of oxygen, said conductor having a layer of an oxide of said metal at said surface, and a thin polymeric coating over said oxide layer and securely adhered to said surface, said coating comprising a polymer produced by glow discharge polymerization of an aliphatic hydrocarbon and having such properties as to permit reduction of oxygen at said electrode by electrons supplied at said surface through said lead and conductor.

2. An oxygen electrode as set forth in claim 1 wherein said coating has a thickness of between about 500 Angstroms and 0.3 $\mu$m.

3. An oxygen electrode as set forth in claim 2 wherein said coating has a thickness of between about 0.1 and about 0.15 $\mu$m.

4. An oxygen electrode as set forth in claim 2 wherein said metal is selected from the group consisting of platinum, gold, palladium, tantalum and iridium.

5. An oxygen electrode as set forth in claim 4 wherein said metal comprises platinum.

6. An oxygen electrode as set forth in claim 5 wherein said oxide layer is predominantly comprised of PtO.

7. An oxygen electrode as set forth in claim 2 wherein said oxide layer is formed by anodization.

8. An oxygen electrode as set forth in claim 2 wherein said polymeric coating is produced by glow discharge polymerization of a monomer selected from the group consisting of ethylene, propylene, butene, methane, ethane, propane and butane.

9. An oxygen electrode as set forth in claim 8 wherein said polymer is cross-linked.

10. An oxygen electrode as set forth in claim 9 wherein said polymer comprises glow discharge polymerized propylene.

11. An oxygen electrode as set forth in claim 10 wherein said polymer contains oxygen.

12. An oxygen electrode as set forth in claim 11 wherein said polymer conforms to the average empirical formula:

$(C_1H_xO_y)$ where x is at least about 1.4 and y is no greater than about 0.2.

13. An oxygen electrode as set forth in claim 2 wherein said coating is of uniform thickness and conforms to the contours of said oxidized surface.

14. An oxygen electrode as set forth in claim 2 wherein said conductor comprises a wire having the crossectional face of one end thereof uncovered by said insulating jacket so as to constitute said surface.

15. An oxygen electrode as set forth in claim 14 wherein said wire has a diameter of not more than about 500 $\mu$m.

16. An oxygen electrode as set forth in claim 15 having an overall diameter of not more than about 1.5 mm.

17. An oxygen electrode as set forth in claim 14 wherein said insulating jacket is comprised of glass.

18. An electrode as set forth in claim 2 wherein said coating is produced by deposition at a rate of between about 25 and about 40 Angstroms of thickness per minute.

19. An electrode as set forth in claim 18 wherein said coating is deposited in said surface in a tubular reactor for which electromagnetic power is generated at a rate of between about 0.2 and about 0.9 KWH per gram of monomer continuously fed thereto.

20. An electrode as set forth in claim 18 wherein said coating is deposited on said surface in a Bell jar reactor for which electromagnetic power is generated at a rate of between about 5 and about 15 KWH per gram of monomer continuously fed thereto.

21. A method for producing an oxygen electrode, adapted for use in polarography, galvanometry or amperometry, that is resistant to poisoning and effective for accurate, reproducible current and voltage measurement, the method comprising the steps of:

generating a plasma from a gas in a low pressure chamber containing the working surface of an oxygen electrode, said electrode comprising a conductor constituted of a metal which catalyzes the cathodic reduction of oxygen, and an insulating jacket that covers all of said conductor except said working surface that is adapted to communicate with an oxygen-containing environment for the cathodic reduction of oxygen, said conductor having a layer of an oxide of said metal at said surface;

introducing an aliphatic hydrocarbon gas into said low pressure chamber;

polymerizing said hydrocarbon by action of said plasma thereon; and depositing a thin adherent coating of said polymer over said oxide layer on said working surface.

22. A method as set forth in claim 21 wherein said polymerization reaction is terminated when the thickness of said polymer coating is between about 500 Angstroms and about 0.3 $\mu$m.

23. A method as set forth in claim 22 wherein said polymerization reaction is terminated when the thickness of said polymer coating is between about 0.1 $\mu$m and about 0.15 $\mu$m.

24. A method as set forth in claim 21 wherein said plasma is generated by introduction of electromagnetic energy into said chamber.

25. A method as set forth in claim 24 wherein said coating is deposited at a rate of between about 25 and about 40 Angstroms of thickness per minute.

26. A method as set forth in claim 25 wherein the polymerization is carried out in a tubular reactor and during polymerization electromagnetic power is generated at a rate of between about 0.2 and about 0.9 KWH per gram of monomer continuously fed thereto.

27. A method as set forth in claim 25 wherein the polymerization is carried out in a Bell jar reactor and during polymerization electromagnetic power is generated at a rate of between about 5 and about 15 KWH per gram of monomer continuously fed thereto.

28. A method as set forth in claim 24 wherein said plasma is generated by inductive coupling at a frequency of between about 1 kilohertz and about 40,000 megahertz.

29. A method as set forth in claim 24 wherein the pressure in said chamber is maintained at between about 10 and about 30 pascals absolute during the polymerization of said hydrocarbon.

30. A method as set forth in claim 24 wherein said gas comprises argon.

31. A method as set forth in claim 21 wherein said aliphatic hydrocarbon is selected from the group consisting of ethylene, propylene, butane, methane, ethane, propane and butane.

32. A method as set forth in claim 31 wherein said aliphatic hydrocarbon comprises propylene.

33. A method as set forth in claim 22 wherein said oxide layer is provided by anodizing said surface.

34. A method as set forth in claim 33 wherein said surface is anodized in a strong oxidizing electrolyte that is substantially free of chloride ion.

35. A method as set forth in claim 34 wherein said surface is anodized in sulfuric acid having a normality of between about 0.5 and about 2.0 at a voltage of between about 1 and about 4 volts D.C. for between about 30 sec. and about 5 minutes.

36. A method as set forth in claim 21 wherein said surface is cleaned and etched by exposure of the surface to argon plasma prior to deposition of said coating.

37. A method as set forth in claim 21 wherein said coating is etched to increase its stability and hydrophilicity by exposing it to an oxygen plasma.

* * * * *